United States Patent [19]

Childress et al.

[11] 4,049,577

[45] Sept. 20, 1977

[54] CATALYST FOR MAKING ACROLEIN

[75] Inventors: David L. Childress, Angleton; William V. Hayes; Richard L. Poppe, both of Clute, all of Tex.

[73] Assignee: The Dow Chemical Company, Midland, Mich.

[21] Appl. No.: 640,616

[22] Filed: Dec. 15, 1975

[51] Int. Cl.$^2$ .................. B01J 21/04; B01J 23/78; B01J 23/84; B01J 27/20
[52] U.S. Cl. ................... 252/443; 252/464; 252/470; 260/604 R; 252/456
[58] Field of Search ............ 260/604 R; 252/456, 252/464, 470, 443

[56] References Cited
U.S. PATENT DOCUMENTS

| | | | |
|---|---|---|---|
| 3,642,930 | 2/1972 | Grasselli et al. | 252/464 X |
| 3,825,502 | 7/1974 | Takenaka et al. | 252/456 |
| 3,907,712 | 9/1975 | O'Hara et al. | 252/470 X |

Primary Examiner—W. J. Shine
Attorney, Agent, or Firm—A. Cooper Ancona

[57] ABSTRACT

A method of preparing acrolein and methacrolein by oxidation of propylene and isobutylene over a new improved catalyst providing conversions and yields, each greater than 90% in a single-pass reactor. The improved catalyst contains within certain prescribed proportions the oxides of cobalt, iron, bismuth, molybdenum, potassium, and optionally silicon. The metals have atomic ratios of $$Co_{3-10}Fe_{0.5-3.0}Bi_{0.5-3.0}Mo_{15}K_{0.01-0.5}Si_{0.5-3.0}$$

and are present in the form of oxides as pellets, spheres, or on a support. With a recycle system, a conversion of the olefin greater than 99% and yield to the aldehyde of greater than 95% are possible.

9 Claims, No Drawings

CATALYST FOR MAKING ACROLEIN

BACKGROUND OF THE INVENTION

Acrolein is a valuable chemical compound useful in the manufacture of various useful unsaturated monomers and chemical intermediates including acrylic acid, acrylonitrile, glycerine and methionine. The principal process of manufacture is by the conversion of propylene by a partial oxidation reaction over a suitable catalyst. Some of the catalysts produce a mixture of acrolein and acrylic acid, while others are highly selective to either the aldehyde or acid. Representative of the former are: U.S. Pat. No. 3,755,434 to Celanese which employs a catalyst containing oxides of molybdenum, cobalt, tellurium and rhodium or boron; U.S. Pat. No. 3,829,476 to Mitsubishi Rayon Co., Ltd. which employs a catalyst containing phosphorus, tungsten, molybdenum, tellurium and combinations of nickel with either cobalt or iron, or cobalt and bismuth or iron and bismuth, and one of potassium or rubidium, all in combination with oxygen. Another patent, to Mitsubishi Rayon Co., Ltd. Japanese Pat. No. 4876804, employs the same combination except that potassium and rubidium are omitted and tin is added. This patent claims a 96% propylene conversion with yields of 85% to acrolein and 6% to acrylic acid.

Representative of the latter catalysts which are primarily selective to the aldehyde are: U.S. Pat. No. 3,755,458, which employs oxides of copper, arsenic, tellurium, and molybdenum or tungsten, and if tellurium is omitted molybdenum is chosen rather than tungsten; and German Pat. No. 2,334,037 to Daicel Ltd. which employs oxides of molybdenum, bismuth, iron, antimony and an alkali metal selected from potassium, rubidium and cesium.

Known catalysts closest to the present invention are disclosed in U.S. Pat. No. 3,855,308, which employs Co, Fe, Bi, W, Mo and Si, Tl and an alkali or alkaline earth metal; and U.S. Pat. No. 3,799,978, which employs Co, Fe, Bi, W, Mo, Si and an alkaline earth metal, both of which are assigned to Nippon Shokubai Kagaku Kogyo Co. Ltd. Another to Rohm & Haas Co., U.S. Pat. No. 3,786,000, employs Mo, Co, Fe, Bi and Sn and optionally one or more of Al, Ni, W, Cr, In and Nb.

Yet another catalyst used in making nitriles issued to Asahi Kasei Kogyo Kabushiki Kaisha (U.S. Pat. No. 3,766,092) employs Mo, Co, Fe, Bi, K and phosphorus. Certain claims of this patent exclude phosphorus as a catalyst component. Other references which employ Mo, Co, Fe, Bi plus at least one other metal which the catalyst of the present invention does not employ are U.S. Pat. Nos. 3,778,386 (Nippon Kayaku Co. Ltd.); 3,825,600 (Nippon Shokubai Kagaku Kogyo, Co. Ltd.); 3,825,502 (Nippon Kayaku Co. Ltd.); 3,761,424 (Deutsche Goldund Silber Scheide anstalt formals Roessler); while U.S. Pat. No. 3,894,091 (Daicel Ltd.) employs Mo, Fe, Bi, K and Sb.

The preparation of the oxidation catalysts employed in processes for making acrolein is generally known to the art and is accomplished by evaporating to dryness either aqueous solutions or suspensions of the salts of the metal components of the catalyst. This may be done in the presence of a support for the catalyst so that the catalytic components are deposited on a carrier or, if unsupported, the resulting solids may be pulverized and subsequently pelleted by compression. A thick slurry or paste of the catalytic components may also be extruded and cut into pellet form. Finally, the supported and unsupported catalytic components are calcined at from about 300° C to 600° C (preferably about 500° C) to form the oxides which are the catalytic components employed in the process. The original componds of the metals are unimportant so long as they form the desired oxides upon calcination. Sometimes the original metal compounds are of such nature that their solutions will co-precipitate, which precipitate is then washed and calcined.

Other methods could be employed such as co-gelling the various ingredients and thereafter drying the gelled mass in a conventional manner; or the solution of gel may be spray dried to form a particulate material which is subsequently compressed into suitable forms or used as is if the particle size is suitable for a fluid bed reactor.

SUMMARY OF THE INVENTION

The present invention resides in a new and improved catalyst for oxidation of propylene to acrolein or isobutylene to methacrolein which provides conversions of the olefin of from about 70% to over 90% and selectivities to the unsaturated aldehyde of from about 85% to over 95%, the remaining products of oxidation being primarily acrylic or methacrylic acid, and carbon oxides, i.e., CO and $CO_2$. The use of the recycle stream as a diluent for the oxygen improves the conversion of propylene to about 99% and the selectivity to acrolein of up to 97%. The recycle stream consists essentially of nitrogen and the carbon oxides. The characteristics of the catalyst permit the recycle stream to be used in place of steam, saving the cost of steam as well as the subsequent separation of water from the product. The oxidation is accomplished in the vapor phase at a temperature of about 295° to 360° C.

The catalyst consists essentially of the oxides of the metals cobalt, iron, bismuth, molybdenum, potassium and optionally silicon, preferably in the form of pellets although it may be supported on alumina, silicon carbide or other suitable material which does not affect the oxidation process. The use of the catalyst on a support generally requires higher temperatures to achieve the same conversions found when using pellets. Operable catalyst compositions are those found within the atomic ratios of $$Co_{3-10}Fe_{0.5-3.0}Bi_{0.5-3.0}Mo_{15.0}K_{0.01-0.5}$$

Optionally silicon can be added in an amount of from about 0.5–3.0 atoms in the above compositions. Preferred catalyst compositions are those containing an atomic ratio of metals within the range of $$Co_{4.5-7.0}Fe_{1-2}Bi_{1-2}Mo_{15}K_{0.5-0.2} \text{ and } Si_{1-1.5}$$

silicon being optional. A particularly preferred catalyst contains metals in the atomic ratio of:

$$Co_{6.37}Fe_{1.35}Bi_{1.3}Mo_{15}K_{0.071}$$

the metals being present as oxides.

The advantages of the present process employing the preferred catalysts are that a high single pass conversion of olefin and high selectivity to the unsaturated aldehyde are provided. Further, the properties of the catalyst permit the use of recycle gas as a diluent which further improves the conversion of olefin and by using the recycle gas in place of the steam employed by the prior art the cost of production is lowered. The present process also permits the use of higher pressure which results in a higher productivity than is obtained by conventional processes.

DETAILED DESCRIPTION OF THE INVENTION

Catalyst Preparation

In preparing the catalyst soluble salts of bismuth, iron and cobalt are placed in solution together, e.g., the nitrates of these metals frequently are dissolved in an acidic aqueous solution. The potassium and molybdenum salts are put into a separate solution and then added to the solution of the other metal salts. The molybdenum salt may be ammonium molybdate [$(NH_4)_6MO_7O_{24}\cdot 4H_2O$] which is the commercial form and potassium is usually added as KOH although any soluble potassium salt, e.g., $KNO_3$, KCl can be added to the ammonium molybdate solution which is slightly basic. When mixing nitrates and ammonium salts one gets a thixotropic solution and this must be allowed to gel before it is dried and pelleted, or gelled on a support and then dried. Thus, thorough mixing is essential to avoid premature gellation and a non-uniform catalyst composition. After the gel is formed, water, is evaporated from the mixture until it contains from about 5 to about 25 percent water. A more preferred water content is from about 8 to about 15 percent. The resulting mixture is then molded into pellets, dried and finally calcined at a temperature within the range of from about 475° to about 530° C. In the calcining operation the catalyst is heated in air for a period of from 4 to 8 hours, gradually increasing the temperature from about 200° C to about 500°–530° C during the first hour and thereafter maintaining a temperature within the range of 500°–530° C for the remainder of the six hours.

The resulting catalyst pellets have a porosity of >60% and contain pores 90% of which are of a size within the range of 0.05 to about 3.0 microns. The surface area of the catalyst preferably is from about 3 to 15 $m^2/g$. At a surface less than about 3 $m^2/g$ the conversion drops to below 90% and at greater than 15 $m^2/g$ a sufficient amount of CO and $CO_2$ is produced so that the economics of the process is adversely affected.

The catalysts made according to the foregoing method are employed to make acrolein from propylene or methacrolein from isobutylene. Other olefins containing up to 6 carbon atoms, however, can be converted to the analogous unsaturated aldehydes over the catalyst of this invention.

Utilization of Catalyst

Parameters employed in the oxidation process are essentially those known to the art. The vapor phase process which can be conducted over the catalyst of the present invention is performed by introducing a gaseous mixture of the olefin, e.g., propylene, together with oxygen (usually as air). An inert diluent, e.g., steam, is generally employed. The preferred duluent for the process of the instant invention is recycled gas which consists of nitrogen, carbon monoxide, carbon dioxide, oxygen and argon. The operable feed composition composition comprises from about 0.2 to about 10 volume percent olefin, about 11.8 to about 20 volume percent oxygen and about 88 to about 70 volume percent of diluent gas. Suitable temperatures are those within the range of 285° C to about 375° C, and contact times can be varied, depending upon the temperature, from about 0.5 to about 5 seconds. Preferred ranges are a feed containing about 4 to about 8 volume percent olefin, about 11 to about 17 volume percent oxygen, and 84 to about 75 volume percent diluent; a temperature of from about 285° C to about 315° C and contact times of from about 1.8 to about 2.8 seconds. Generally, increasing the pressure on the feed decreases both conversion and selectivity of the catalyst. Desirable pressures are from about 10 to about 85 psig, while the preferred range is from about 25 to about 75 psig.

The minor amounts of unsaturated acid produced in the process are of no consequence since the product aldehyde most frequently is oxidized further to the acid by employing a catalyst which is highly selective for the oxidation of an aldehyde to the analogous acid and the by-product acid is carried on through this second oxidation and recovered from the effluent stream thereof along with the acid produced in this step. If it is desired to use the aldehyde in some other process in which the acid would be undesirable, the acid can be separated by merely distilling off the aldehyde which boils at a considerably lower temperature than the acid.

One of the catalysts of the prior art which uses tungsten in addition to the catalytic components of the instant invention was employed using nitrogen in place of the steam ordinarily employed in the prior art process to make acrolein from propylene. In a comparison with the instant catalyst it was observed to have equally good selectivity but only about half the conversion of the propylene as that of the instant catalyst.

EXAMPLE 1

Preparation of Pelleted Catalyst

Solution A was made by dissolving 344.6 grams of bismuth nitrate in 1200 mls of distilled water to which 75 mls of concentrated nitric acid had been added; to the resulting solution 258.4 gms of ferric nitrate and 1014 gms of cobalt nitrate were added. Solution B was made by dissolving 1448 gms of ammonium molybdate in 2750 mls of water and heat (about 90° C) and stirring. After the ammonium molybdate was dissolved, 2.18 gms of potassium hydroxide were added. A thixotropic material was formed by mixing solution A and B together with stirring. Excess water was removed from heat (about 100° C) to a 9.6 wt. percent free water level (90.4% solids). The resulting catalyst material was formed into cylindrical pellets by pressing into ⅜-inch Teflon plastic sheets drilled with ¼-inch holes. The filled molds were oven-dried (about 150° C) for 1 hour and the cylindrical catalyst pellets blown from mold with low air pressure. The pellets were then calcined in an air furnace at about 200° C for 20 minutes, after which the furnace temperature was increased in about 50° C-increments, every 20 minutes until 515° C was attained. Catalyst was held at 515° C for 4 hours. This resulted in a catalyst having a surface area of 7.0 $m^2/g$, 85% of the pores being in the range of 0.2 to 5 microns in diameter. The atomic ratio of the metal elements in the catalyst composition was as follows:

$$Mo_{15}Co_{6.37}Bi_{1.3}Fe_{1.35}K_{0.071}$$

EXAMPLE 2

Preparation of Supported Catalyst

Solution A was made by (1) dissolving 30.2 gms of bismuth nitrate in 250 mls of distilled water containing 13 mls of concentrated nitric acid; to this was added (2) 25.2 gms of ferric nitrate and 72.5 gms of cobalt nitrate. Solution A was added, with stirring, to 500 cc's of preheated (150° C) carrier* and dried one hour in a 150° C oven. Solution B was made by (1) dissolving (with heat and stirring) 148.4 gms of ammonium molybdate in 300 mls of distilled water. Stirring and heating was continued until cloudiness just appears (past this cloud point a gel occurs and the solution cannot be used) and (2) a second solution was made by adding 2.09 gms of 10% potassium hydroxide solution to 50 mls of distilled water and adding 16.8 gms of Ludox L.S. (a 30% colloidal solution of silica) and (3) solutions made in (1) and (2) above were added together. Solution B was then added to the nitrate-coated (Solution A) carried with stirring and stirred on coated (Solution A) carrier with stirring and stired on a steam bath until excess water was removed. The carrier, now impregnated with catalyst salts, was placed in an oven at 150° C until dry. The catalyst was calcined in an air-furnace at 300° C for 20 minutes, 400° C for 20 minutes and 425° C for 5 hours and then removed and cooled. This resulted in a catalyst having a surface area of 1.7 m²/g, 90% of the pores being in the range of 0.05 to 5 microns in diameter. The atomic ratio of the metals in the resulting catalyst was as follows:

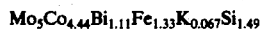

$Mo_5Co_{4.44}Bi_{1.11}Fe_{1.33}K_{0.067}Si_{1.49}$

Also useful as supports are those having a surface area of from about 0.2 to 2 m²/g and a porosity wherein about 90% of the pores contained therein are within the range of from about 50 to about 1500 microns in diameter.

*The carrier was alumina (SA-5205, Norton Co.) having a surface area of <1 m²/g, 90% of the pores being in the range of 50 to 420 microns in diameter.

Utilizationn of Catalyst

EXAMPLE 3

A volume of 1000 mls of the catalyst pellets (3/16 $d$ × ⅛ inch l) prepared as in Example 1 was placed in a 1-inch stainless steel tubular reactor. The tube was heated to 305° C and a gaseous mixture of 5.2 volume percent propylene, 60.8 volume percent air, and 34 volume percent diluent (nitrogen) was passed through the tube with a contact time of 2.6 seconds. The single pass propylene conversion was 93.5% with selectivities to acrolein and acrylic acid of 86.4% and 5.7%, respectively.

EXAMPLE 4

Into a stainless steel tubular jacketed reactor ⅝-inch I.D. was placed 260 mls of the supported catalyst prepared in Example 2. The tube was heated to 345° C (by employing a heat transfer medium in the jacket) and a gaseous mixture of 5.2 volume percent propylene, 67.7 volume percent air and 26.7 volume percent diluent ($N_2$) was passed through the tube with a contact time of 2.4 seconds. A one-pass propylene conversion of 86% and selectivity to acrolein of 94% and to acrylic acid of 3.0% was obtained.

EXAMPLES 5–16

Catalysts made in the manner of Examples 1 and 2 having different atomic ratios were prepared as in Example 3 (except Example 15) and tested as in Example 4. Table I shows the catalyst composition, temperatures and contact times at which the reaction was conducted and the resulting conversion of propylene and selectivity to acrolein and acrylic acid.

TABLE I

| Example Number | Catalyst Composition | | | | | | Temp. (° C) | Time (sec) | Conversion (%$C_3H_6$) | Selectivity (%) | | |
| | Mo | Co | Fe | Bi | K | Si | | | | Acrolein | Acrylic | Carbon Oxides |
|---|---|---|---|---|---|---|---|---|---|---|---|---|
| 5 | 15 | 4.6 | 1.35 | 1.3 | 0.07 | 1.3 | 310 | 2.6 | 86.4 | 92.9 | 0.13 | 6.97 |
| 6 | 15 | 5.2 | 1.35 | 1.3 | 0.07 | — | 315 | 2.5 | 93.0 | 88.7 | 7.01 | 4.29 |
| 7 | 15 | 6.4 | 1.35 | 1.3 | 0.07 | — | 310 | 1.6 | 90.5 | 92.2 | 5.4 | 1.1 |
| 8 | 15 | 7.0 | 1.35 | 1.3 | 0.07 | — | 300 | 2.7 | 93.4 | 92.0 | 5.1 | 2.9 |
| 9 | 15 | 4.6 | 1.35 | 1.3 | 0.07 | — | 295 | 2.3 | 92.9 | 91.0 | 3.7 | 5.3 |
| 10 | 15 | 4.6 | 1.35 | 1.66 | 0.07 | — | 300 | 2.7 | 79.8 | 91.1 | 4.7 | 4.2 |
| 11 | 15 | 4.6 | 1.73 | 1.3 | 0.07 | — | 340 | 2.5 | 78.8 | 91.2 | 5.0 | 3.8 |
| 12 | 15 | 7.0 | 2.03 | 1.96 | 0.11 | — | 315 | 2.7 | 87.6 | 93.1 | 3.6 | 3.3 |
| 13 | 15 | 5.7 | 1.66 | 1.6 | 0.09 | — | 300 | 2.7 | 92.5 | 91.4 | 4.8 | 3.8 |
| 14 | 15 | 5.0 | 1.0 | 1.3 | 0.07 | 1.3 | 315 | 2.9 | 92.8 | 91.8 | 5.2 | 3.0 |
| 15 | 15 | 4.44 | 1.28 | 1.97 | 0.064 | 1.5 | 375 | 2.7 | 73 * | 91 | 3.2 | 4.0 |
| 16 | 15 | 4.64 | 1.35 | 1.3 | 0.07 | — | 295 | 2.3 | 90 | 90 | 5.1 | 4.2 |

*This catalyst is a supported catalyst made according to Example 2.

COMPARATIVE EXAMPLES

In order to show the necessity of each of the promotor components added to the molybdenum, catalyst compositions identical to that of Example 5, save for one element, were run. Comparative results with catalysts not within the scope of the present invention are shown in Table II.

Conversions of propylene were extremely low and carbon oxide production was high for catalysts in which cobalt, iron or bismuth was omitted while the catalyst in which potassium was omitted gave high conversion, but low selectivity and high carbon oxide production.

TABLE II

| Number | Catalyst Composition | | | | | | Temp. (° C) | Time (sec) | Conversion (%$C_3H_6$) | Selectivity (%) | | |
| | Mo | Co | Fe | Bi | K | Si | | | | Acrolein | Acrylic | Carbon Oxides |
|---|---|---|---|---|---|---|---|---|---|---|---|---|
| 17 | 15 | — | 1.35 | 1.3 | 0.07 | 1.3 | 327 | 2.7 | 13.7 | − 76.2 | 0 | 22.6 |
| 18 | 15 | 4.6 | — | 1.3 | 0.07 | 1.3 | 325 | 2.7 | 3.5 | 83.6 | 0 | 14.4 |
| 19 | 15 | 4.6 | 1.35 | — | 0.07 | 1.3 | 300 | 2.7 | 14.5 | 85.2 | 0 | 14.2 |

TABLE II-continued

| Number | Catalyst Composition | | | | | | Temp. (°C) | Time (sec) | Conversion (%C₃H₆) | Selectivity (%) | | |
|---|---|---|---|---|---|---|---|---|---|---|---|---|
| | Mo | Co | Fe | Bi | K | Si | | | | Acrolein | Acrylic | Carbon Oxides |
| 20 | 15 | 4.6 | 1.35 | 1.3 | — | 1.3 | 300 | 2.7 | 90.5 | 75.5 | 5.8 | 18.1 |

EXAMPLE 21

In a similar manner isobutylene (IB) was passed over the catalyst composition of Example 7, Table I, to obtain methacrolein. The catalyst was a ¼ inch $d$ × ¼ inch l pellet, having a surface area of 8.7 m²/g, a porosity of 66%, 83% of the pores being between 0.1 and 3 microns. The olefin concentration in the feed was about 6.4 volume percent, oxygen was about 13–14 volume percent and nitrogen diluent was about 80–81 volume percent. For comparison propylene was passed over the same catalyst, the concentration in the feed stream being about 5.7 volume percent propylene, about 13.0 volume percent oxygen and about 81 volume percent nitrogen diluent. The reaction temperature, contact time and results obtained are given in Table III.

TABLE III

| Olefin | Temp (°C) | Time (sec) | IB Conversion (%)* | Selectivity (%) | | |
|---|---|---|---|---|---|---|
| | | | | Aldehyde | Acid | CO&CO₂ |
| Isobutylene | 325 | 2.0 | 95.6 | 88.9 | 4.6 | 6.5 |
| Isobutylene | 335 | 2.0 | 98.2 | 86.2 | 5.0 | 8.8 |
| Isobutylene | 325 | 2.5 | 95.5 | 88.5 | 4.5 | 7.0 |
| Propylene | 294 | 2.3 | 94.2 | 91.5 | 5.9 | 2.3 |

*Conversion obtained is from a single pass

The preferred catalysts of this invention are those exemplified in Table I, with those most preferred being the pelleted catalysts, i.e., non-supported.

The catalysts of the present invention when employed in a single pass system can achieve productivities of up to about 800 lbs/day/ft³ (12814 kg/day/m³) of catalyst.

We claim:

1. An improved catalyst for the oxidation of a lower olefin containing 3 to 6 carbon atoms to the analogous unsaturated aldehyde which consists essentially of oxides of cobalt, iron, bismuth, molybdenum and potassium wherein the atomic ratios of the metals are within the ranges $$Co_{4.5-7.0}Fe_{1-2}Bi_{1-2}Mo_{15}K_{0.05-0.2}.$$

2. A method for making an improved oxidation catalyst pellet containing oxides of cobalt, iron, bismuth, molybdenum, and potassium which comprises:
   1. making a first solution of the compounds of cobalt, iron and bismuth,
   2. making a second solution of the compounds of molybdenum and potassium,
   3. mixing thoroughly said first and second solutions,
   4. removing excess water until a moldable clay-like mixture is produced,
   5. forming said clay-like mixture into a mold to produce catalyst particles,
   6. drying the molded catalyst in the mold,
   7. removing the dried catalyst from the mold and calcining it in air for a period of about 6 hours, wherein the calcination temperature is gradually increased from about 200° C to about 500° C during the first hour and the temperature is maintained at about 500° C for the remaining time,
   8. cooling the so-formed oxidation catalyst prior to use.

3. A method for making an improved supported oxidation catalyst which contains the oxides of cobalt, iron, bismuth, molybdenum and potassium which comprises:
   1. making a first solution of the compounds of cobalt, iron and bismuth,
   2. absorbing said first solution on a catalyst support,
   3. drying said support containing the adsorbed first solution,
   4. making a second solution of the compounds of molybdenum potassium,
   5. absorbing said second solution on said catalyst support containing said absorbed first solution,
   6. drying said support containing said absorbed first and second solutions,
   7. calcining the dried catalyst support in air for a period of about 6 hours, wherein the calcination temperature is gradually increased from about 200° C to about 500° C during the first hour and the temperature is maintained at about 500° C for the remaining time,
   8. cooling the so-formed supported oxidation catalyst prior to use.

4. The method of claim 2 wherein the compounds of cobalt, iron and bismuth in said first solution are nitrates, the molybdenum compound in said second solution is a soluble molybdate and the potassium compound is potassium hydroxide.

5. The method of claim 3 wherein the compounds of cobalt, iron and bismuth in said first solution are nitrates, the molybdenum compound in said second solution is a soluble molybdate and the potassium compound is potassium hydroxide.

6. The method of claim 3 wherein the catalyst support is selected from the group consisting of silicon carbide and alumina.

7. The method of claim 6 wherein the catalyst support has a surface area of from about 0.2 to about 2 m²/g and a porosity wherein about 90% of the pores contained therein are within the range of from about 50 to about 1500 microns in diameter.

8. The product made by the process of claim 6 wherein the atomic ratios of the metals of the catalytic coating are within the ranges of $$Co_{4.5-7}Fe_{1-2}Bi_{1-2}Mo_{15}K_{0.05-2}.$$

9. The product made by the process of claim 7 wherein the atomic ratios of the metals of the catalytic coating are within the range of $$Co_{4.5-7}Fe_{1-2}Bi_{1-2}Mo_{15}K_{0.05-0.2}.$$

* * * * *

UNITED STATES PATENT AND TRADEMARK OFFICE
CERTIFICATE OF CORRECTION

PATENT NO. : 4,049,577
DATED : September 20, 1977
INVENTOR(S) : David L. Childress, et al It is certified that error appears in the above-identified patent and that said Letters Patent are hereby corrected as shown below:

Col. 2, Line 5 - the word "componds" should be--compounds--

Col. 2, Line 13 - after "solution" the word "of" should be--or--.

Col. 2, Line 40 - insert between "not" and "affect" the word--itself--.

Col. 2, Lines 47 and 53 - in the formula the symbols "CO" and "MO" should be--Co-and-Mo--.

Col. 2, Line 57 - in the formula "MO" should be--Mo--.

Col. 3, Line 15 - in the formula "MO" should be--Mo--.

Col. 4, Line 44 - after water the word "and" should be --with--.

Col. 5, Line 20 - the phrase "carried with stirring and stirred on coated (Solution A)" should be deleted.

Col. 5, Line 22 - the word "stired" should be --stirred--.

Col. 5, Line 47 - in the formula the subscript for Mo should be--15--.

UNITED STATES PATENT AND TRADEMARK OFFICE
CERTIFICATE OF CORRECTION

PATENT NO. : 4,049,577

DATED : September 20, 1977

INVENTOR(S) : David L. Childress, et al

It is certified that error appears in the above-identified patent and that said Letters Patent are hereby corrected as shown below:

Col. 5, Lines 60 and 61 - in the parentheses "(3/16 d x 1/4 inch 1)" should be--(3/16"d x 1/4"1)--.

Col. 7, Line 42 - "An improved catalyst" should be--An improved pelleted, unsupported catalyst--.

Col. 8, Line 17 - the word "adsorbed" should be--absorbed--.

Col. 8, Line 20 - the word--and--should occur between "molybdenum" and "potassium".

Col. 8, Line 62 - in the formula the subscript for K should be--0.05-0.2--.

Signed and Sealed this

Fourteenth Day of March 1978

[SEAL]

Attest:

RUTH C. MASON
*Attesting Officer*

LUTRELLE F. PARKER
*Acting Commissioner of Patents and Trademarks*